US010524750B2

(12) United States Patent
Hsieh et al.

(10) Patent No.: US 10,524,750 B2
(45) Date of Patent: Jan. 7, 2020

(54) SCANNING SYSTEM

(71) Applicant: Institute of Nuclear Energy Research, Atomic Energy Council, Executive Yuan, R.O.C., Taoyuan (TW)

(72) Inventors: Ho-Hui Hsieh, Taoyuan (TW); Sheng-Pin Tseng, Taoyuan (TW); Syuan-Ya Huang, Taoyuan (TW)

(73) Assignee: INSTITUTE OF NUCLEAR ENERGY RESEARCH, ATOMIC ENERGY COUNCIL, EXECUTIVE YUAN, R.O.C, Taoyuan (TW)

( * ) Notice: Subject to any disclaimer, the term of this patent is extended or adjusted under 35 U.S.C. 154(b) by 151 days.

(21) Appl. No.: 15/723,502

(22) Filed: Oct. 3, 2017

(65) Prior Publication Data
US 2019/0008471 A1    Jan. 10, 2019

(30) Foreign Application Priority Data
Jul. 7, 2017    (TW) .............................. 106122923 A

(51) Int. Cl.
*A61B 6/00* (2006.01)
*A61B 6/04* (2006.01)
*A61B 6/02* (2006.01)

(52) U.S. Cl.
CPC ............ *A61B 6/4447* (2013.01); *A61B 6/025* (2013.01); *A61B 6/0407* (2013.01); *A61B 6/4476* (2013.01); *A61B 6/02* (2013.01)

(58) Field of Classification Search
CPC ..... A61B 6/4447; A61B 6/025; A61B 6/0407; A61B 6/0457; A61B 6/4435; A61B 6/4476; A61B 6/02

USPC ......................................................... 378/197
See application file for complete search history.

(56) References Cited

U.S. PATENT DOCUMENTS

| 5,768,336 A * | 6/1998 | Khutoryansky ......... A61B 6/00 378/116 |
| 7,478,947 B2 * | 1/2009 | Kobayashi ........... A61B 6/0457 378/167 |
| 2001/0040939 A1 * | 11/2001 | Kobayashi ............. G03B 42/02 378/177 |
| 2002/0003864 A1 * | 1/2002 | Katoh ................... A61B 6/4233 378/197 |
| 2002/0006184 A1 * | 1/2002 | Katoh ...................... A61B 6/02 378/196 |
| 2002/0051517 A1 * | 5/2002 | Schwieker ........... A61B 6/4429 378/196 |
| 2002/0080921 A1 * | 6/2002 | Smith .................. A61B 6/0457 378/189 |

(Continued)

*Primary Examiner* — Taeho Jo
(74) *Attorney, Agent, or Firm* — Locke Lord LLP; Tim Tingkang Xia, Esq.

(57) ABSTRACT

A scanning system includes a first base, a bed panel, a bed board, a second base and an X-ray mechanism. The bed panel, movably located on the first base, includes a first image-receiving module. The bed board is movably located on the bed panel. The second base, located aside to the first base, includes a second image-receiving module. The X-ray mechanism, connected with the first base, includes an X-ray tube. While the bed panel and the bed board are moved away from the second base, and the X-ray mechanism is moved toward the second base; then, the X-ray tube would undergo a vertical movement to a position aside to a lateral side of the first base by facing the second base.

12 Claims, 6 Drawing Sheets

(56) References Cited

U.S. PATENT DOCUMENTS

| | | | | |
|---|---|---|---|---|
| 2005/0281387 A1* | 12/2005 | Kusch | .................. | A61B 6/00 |
| | | | | 378/197 |
| 2005/0281389 A1* | 12/2005 | Kusch | .................. | A61B 6/4441 |
| | | | | 378/197 |
| 2009/0257561 A1* | 10/2009 | Okuno | .................. | A61B 6/4233 |
| | | | | 378/116 |
| 2010/0008474 A1* | 1/2010 | Hornung | .................. | A61B 6/4233 |
| | | | | 378/197 |
| 2010/0232574 A1* | 9/2010 | Ahn | .................. | A61B 6/447 |
| | | | | 378/167 |
| 2011/0311031 A1* | 12/2011 | Yoshida | .................. | A61B 6/04 |
| | | | | 378/197 |
| 2013/0039465 A1* | 2/2013 | Okuno | .................. | A61B 6/08 |
| | | | | 378/62 |
| 2013/0235983 A1* | 9/2013 | Okuno | .................. | A61B 6/06 |
| | | | | 378/197 |
| 2014/0241510 A1* | 8/2014 | Wang | .................. | G08C 17/02 |
| | | | | 378/197 |
| 2014/0321621 A1* | 10/2014 | Lee | .................. | H05G 1/02 |
| | | | | 378/197 |
| 2015/0117609 A1* | 4/2015 | Tonotsuka | .................. | A61B 6/4476 |
| | | | | 378/62 |
| 2016/0073985 A1* | 3/2016 | Moon | .................. | A61B 6/447 |
| | | | | 378/181 |
| 2016/0081650 A1* | 3/2016 | Okusu | .................. | A61B 6/56 |
| | | | | 378/62 |

\* cited by examiner

SCANNING SYSTEM

CROSS REFERENCE TO RELATED APPLICATION

This application claims the benefit of Taiwan Patent Application Serial No. 106122923, filed Jul. 7, 2017, the subject matter of which is incorporated herein by reference.

BACKGROUND OF THE INVENTION (1) Field of the Invention

The invention relates to a scanning system, and more particularly to the scanning system that is furnished with an improved X-ray bed-panel mechanism.

(2) Description of the Prior Art

In the art, medical routine radiography applies typically an X-ray to project or radiate a specific part of a human body. Since various organs and, possible, different diseases exist in a human body at the same time to contribute different transmittances of the X-ray, thus such a feature in varying transmittances is utilized to depict a corresponding shadow image for medical diagnosis. Generally speaking, to process the routine radiography, at least a medical X-ray imaging apparatus is required. This X-ray imaging apparatus includes at least a set of X-ray sources and a set of image-receiving devices. For a successful diagnosis through medical imaging, plenty of X-ray images upon specific human tissues at different directions are required. In order to achieve relevantly multi-directional X-ray images, the X-ray imaging apparatus needs to displace the X-ray sources and/or the image-receiving devices frequently, or to include at least two sets of X-ray sources and/or at east two sets of image-receiving devices. Particularly, the patient to be tested shall change his/her body states accordingly, such that the corresponding multi-directional X-ray images can be obtained for respective diagnosis.

As described above, the multi-directional X-ray images of routine radiography can be obtained by varying purposely patient's body states, such as standing, lying, sitting and the like. In particular, the standing state usually requires a second set of the image-receiving device to capture the image. The lying state is achieved by having the patient to lie down on a bed board. Clinically, the lying and standing states are the basic states for most of the routine radiography, and particular states are generally derived from these two states by slightly adjusting patient's body. Hence, in most medical facilities, patients would be designated to different X-ray imaging apparatuses according to the states they need for the routine radiography.

Thus, an improvement upon the conventional X-ray imaging apparatus that can be applicable to both the standing state and the lying state is definitely welcome to the art.

SUMMARY OF THE INVENTION

Accordingly, it is an object of the present invention to provide a scanning system that can operate conveniently between a bed-board imaging mode and a lateral imaging mode.

In the present invention, the scanning system includes a first base, a bed panel, a bed board, a second base and an X-ray mechanism. The bed panel, movably located on the first base, includes a first image-receiving module. The bed board is movably located on the bed panel. The second base, located aside to the first base, includes a second image-receiving module. The X-ray mechanism, connected with the first base, includes an X-ray tube. While the bed panel and the bed board are moved away from the second base, and the X-ray mechanism is moved toward the second base; then, the X-ray tube would undergo a vertical movement to a position aside to a lateral side of the first base by facing the second base.

As stated above, the scanning system provided by the present invention is a grounded X-ray imaging apparatus that can be easily switched to work in either the bed-panel imaging mode or the lateral imaging mode. Thereupon, clinical lying/standing scan upon the head, the neck, the body and the limbs, can be performed at the same system, either for the routine radiography or for the 3D digital tomosynthesis.

All these objects are achieved by the scanning system described below.

BRIEF DESCRIPTION OF THE DRAWINGS

The present invention will now be specified with reference to its preferred embodiment illustrated in the drawings, in which.

DESCRIPTION OF THE PREFERRED EMBODIMENT

Figure 1:
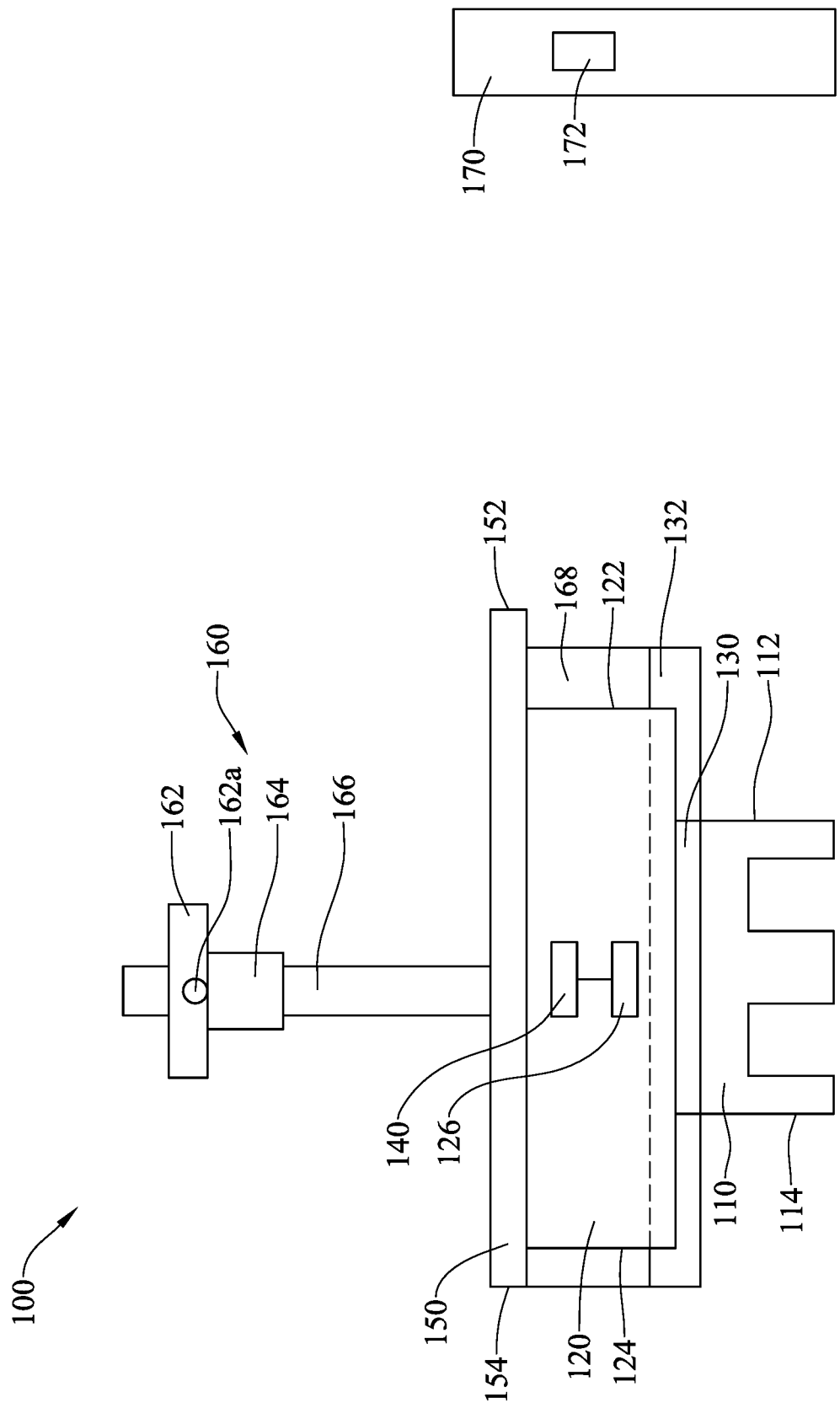
FIG. 1 is a schematic view of a preferred scanning system in accordance with the present invention, in a first operation state.

The invention disclosed herein is directed to a scanning system. In the following description, numerous details are set forth in order to provide a thorough understanding of the present invention. It will be appreciated by one skilled in the art that variations of these specific details are possible while still achieving the results of the present invention. In other instance, well-known components are not described in detail in order not to unnecessarily obscure the present invention.

Referring now to FIG. 1 through FIG. 6, six operation states of a preferred scanning system in accordance with the present invention are schematically shown, respectively.

In this embodiment, the scanning system 100 includes a first base 110, a bed panel 120, a bed board 150, an X-ray mechanism 160 and a second base 170.

The bed panel 120 is movably disposed on the first base 110. The X-ray mechanism 160 is movably connected with the first base 110. In details, the first base 110 has two opposing lateral sides 112, 114. The bed panel 120 has also two opposing lateral sides 122, 124 and an position-adjusting mechanism 126. The first base 110 includes a first displacement mechanism 130 and a second displacement mechanism 132. The first displacement mechanism 130 is used to displace the bed panel 120, while the second displacement mechanism 132 is used to displace the X-ray mechanism 160. In one exemplary example, the first displacement mechanism 130 and the second displacement mechanism 132 are embodied as individual sliding slots, while the bed panel 120 and the X-ray mechanism 160 are embodied to have respective sliding rails. Thereupon, the bed panel 120 can then move with respect to the first base 110 by the sliding motion between the sliding slot of the first displacement mechanism 130 and the corresponding sliding rail on the bed panel 120. Similarly, the X-ray mechanism 160 can utilize its own sliding rail to slide along the sliding slot of the second displacement mechanism 132. In addition, in another exemplary example, the first displacement mechanism 130 and the second displacement mechanism 132 are embodied as individual sliding rails, while the bed panel 120 and the X-ray mechanism 160 are embodied to have respective sliding slots. Further, the aforesaid position-adjusting mechanism (the rail-slot pair or the slot-rail pair) can be alternatively embodied as a screwing mechanism. Nevertheless, it should be understood that the embodiment of the position-adjusting mechanism is not limited to any of the aforesaid exemplary examples. Practically, any mechanism able to slide individually the bed panel 120 and the X-ray mechanism 160 with respect to the first base 110 can be a qualified position-adjusting mechanism of the present invention. In particular, the first displacement mechanism 130 and the second displacement mechanism 132 for driving the bed panel 120 and the X-ray mechanism 160, respectively, can be also human-powered. In some other exemplary examples, the first displacement mechanism and the second displacement mechanism may drive electrically the bed panel 120 and the X-ray mechanism 160, respectively!

The first image-receiving module 140, located in the bed panel 120, can be a digital flat-panel detector for receiving X-ray signals generated by the X-ray mechanism 160 for further forming an image. The first image-receiving module 140 is connected with the position-adjusting mechanism 126. The position-adjusting mechanism 126, located inside the bed panel 120, is also connected with the bed panel 120. The position-adjusting mechanism 126 drives the first image-receiving module 140 to an optimal scan position by matching the X-ray sources. In the present invention, embodying of the position-adjusting mechanism 126 is not limited to the aforesaid mechanism, but to any mechanism that can serve the first image-receiving module 140 to achieve its desired function. For example, the position-adjusting mechanism 126 of the present invention can be a pair of a sliding rail and a sliding slot, a screwing mechanism, or a screw-bar mechanism. In some other embodiments, the position-adjusting mechanism may also move the first image-receiving module in an electrical manner.

The bed board 150, movably located on the bed panel 120, has two opposing lateral sides 152, 154. As shown in FIG. 1, a length of the bed board 150 is larger than that of the bed panel 120, and the length of the bed panel 120 is larger than that of the first base 110.

The X-ray mechanism 160, movably connected with the first base 110, includes an X-ray tube 162, an emission window 162a, a collimator 164, a pillar 166 and a bottom frame 168.

The bottom frame 168 is connected to the second displacement mechanism 132 of the first base 110, where the second displacement mechanism 132 is used to move the X-ray mechanism 160. The pillar 166 is connected to the bottom frame 168, and the X-ray tube 162 is movably located at the pillar 166. The collimator 164 is connected with the X-ray tube 162 in a co-moving manner. The X-ray signal generated by the X-ray tube 162 is emitted through the emission window 162a and further out through the collimator 164. In this embodiment, the X-ray tube 162 is applied for the routine radiography or the 3D digital tomosynthesis.

The second base 170, located aside to the first base 110, includes the second image-receiving module 172, where the second image-receiving module 172 can be an upright digital flat-panel detector, an X-ray film cartridge, a digital photostimulable phosphor plate or a handheld digital flat-panel detector.

Upon such an arrangement as shown in FIG. 1, the bed-panel imaging mode can be provided.

To process a test of the bed-panel imaging mode, the patient to be imaged is firstly lay down on the bed board 150, then the bed board 150 is shifted to an imaging position, then the X-ray mechanism 160 is moved to locate the X-ray tube 162 at a position corresponding to the aforesaid imaging position, and finally the first image-receiving module 140 is displaced by the position-adjusting mechanism 126 to a corresponding image-forming position for co-operating the X-ray tube 162. In one example, the patient is thus ready for static imaging of the routine radiography. In another example, the patient is also set for a continuous X-ray motion scan. After the motion scan, a 3D image can be formed by reconstructing data collected from the motion scan (i.e. a 3D digital tomosynthesis).

In this embodiment as shown in FIG. 1, a lateral imaging mode can be also provided. To switch the scanning system 100 from the bed-panel imaging mode to the lateral imaging mode, follow description is provided by accompanying FIG. 1 through FIG. 6.

Figure 2:
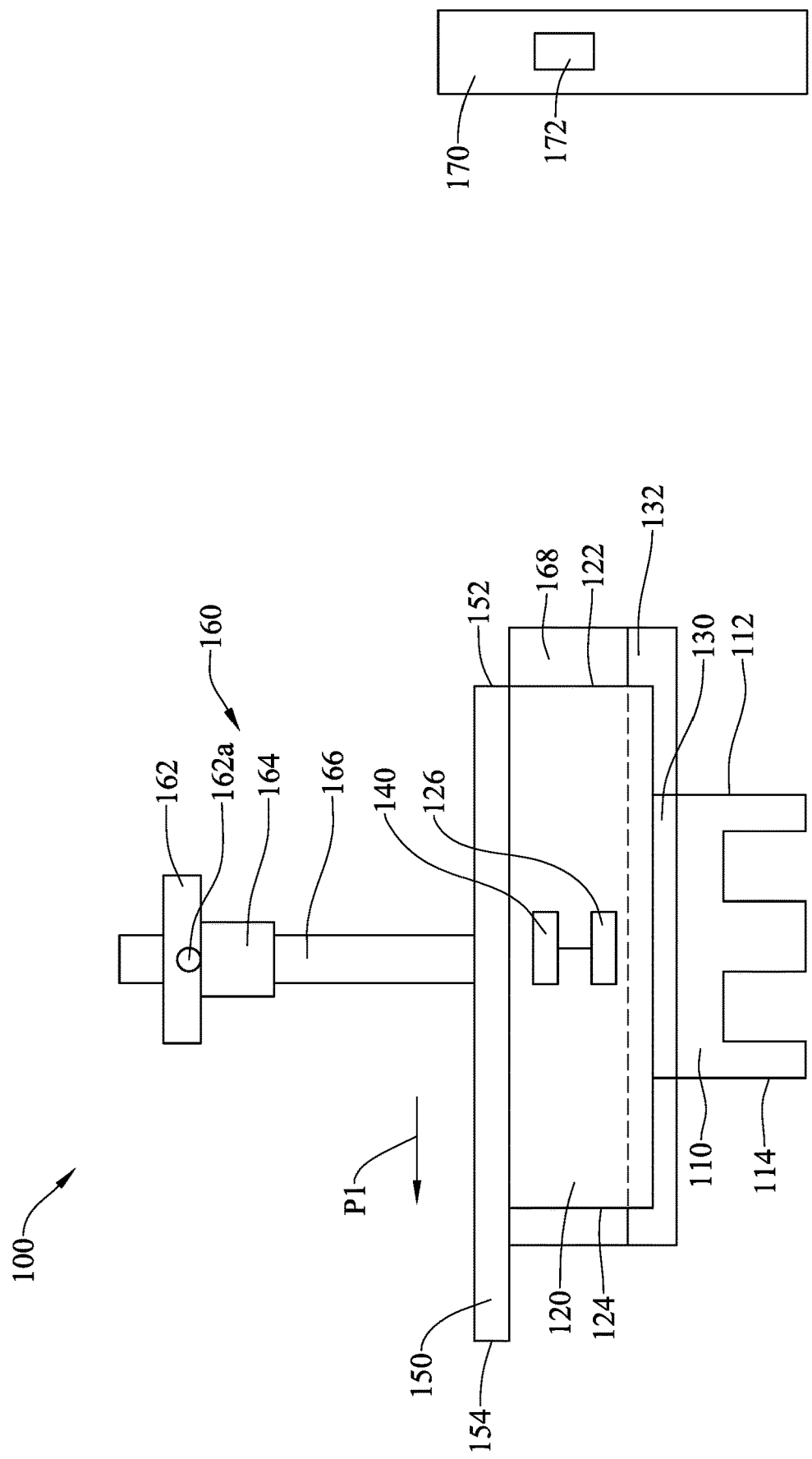
FIG. 2 shows a second operation state of FIG. 1.
Figure 3:
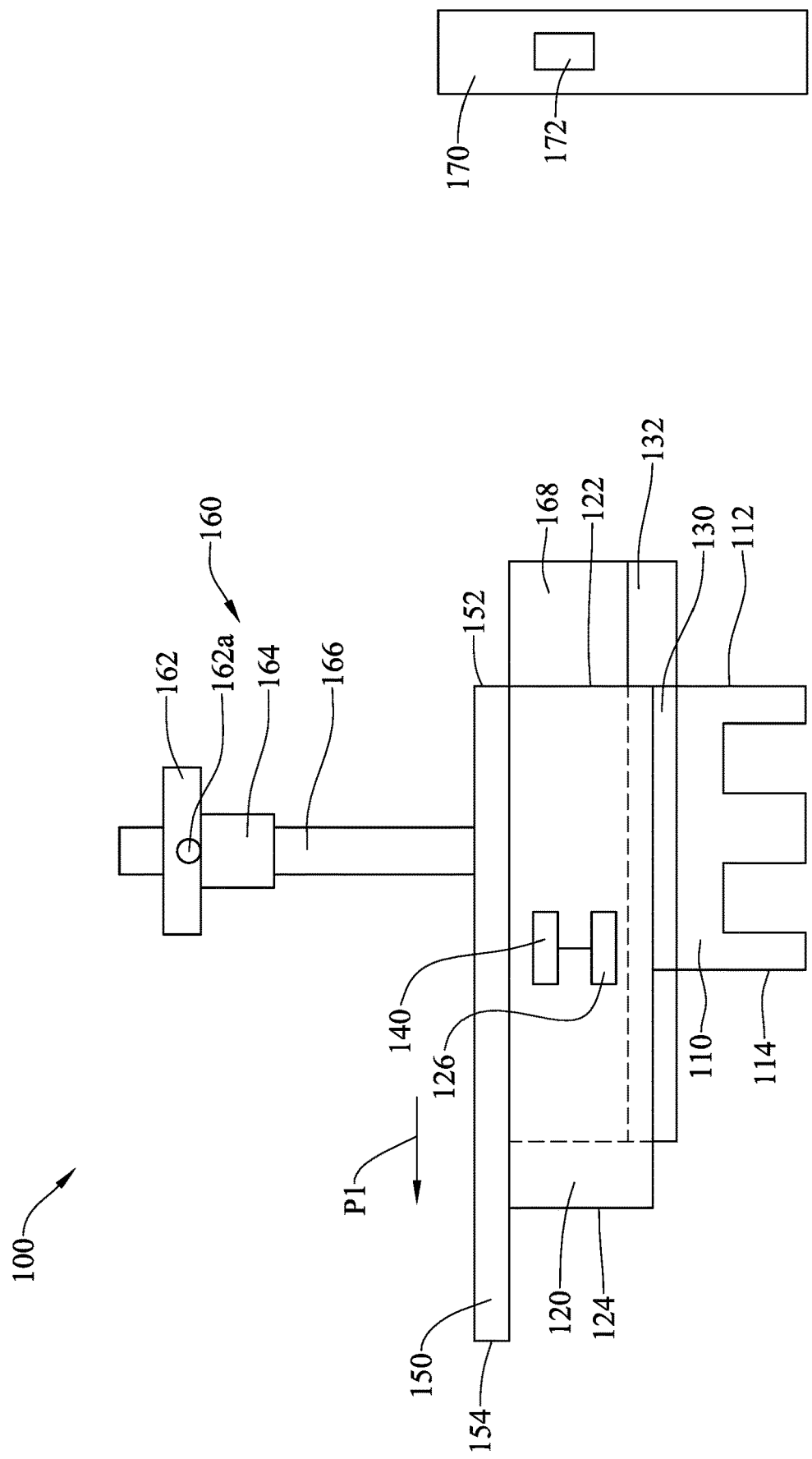
FIG. 3 shows a third operation state of FIG. 1.

As shown in FIG. 2 and FIG. 3, the bed panel 120 and the bed board 150 are moved away from the second base 170 in a P1 direction. In details, the bed board 150 are firstly moved away from the second base 170 in the P1 direction so as, but not limited, to align a lateral side 152 of the bed board 150 with a lateral side 122 of the bed panel 120 (as shown in FIG. 2). In some other embodiments not shown here, the lateral side 152 of the bed board 150 is no need of being flush with the lateral side 122 of the bed panel 120, but the bed board 150 needs to move in the P1 direction P1 according to the present invention. Then, the bed panel 120 and the bed board 150 are synchronously moved away from the second base 170 in the P1 direction so as, but not limited, to have another lateral side 152 of the bed board 150 and another lateral side 122 of the bed panel 120 to align with a lateral side 112 of the first base 110, respectively (as shown in FIG. 3). In some other embodiments not shown here, the another lateral side 152 of the bed board 150 and the another lateral side 122 of the bed panel 120 are not flush with the lateral side 122 of the bed panel 120, but the bed board 150 and the bed panel 120 need to move in the P1 direction according to the present invention.

Figure 4:
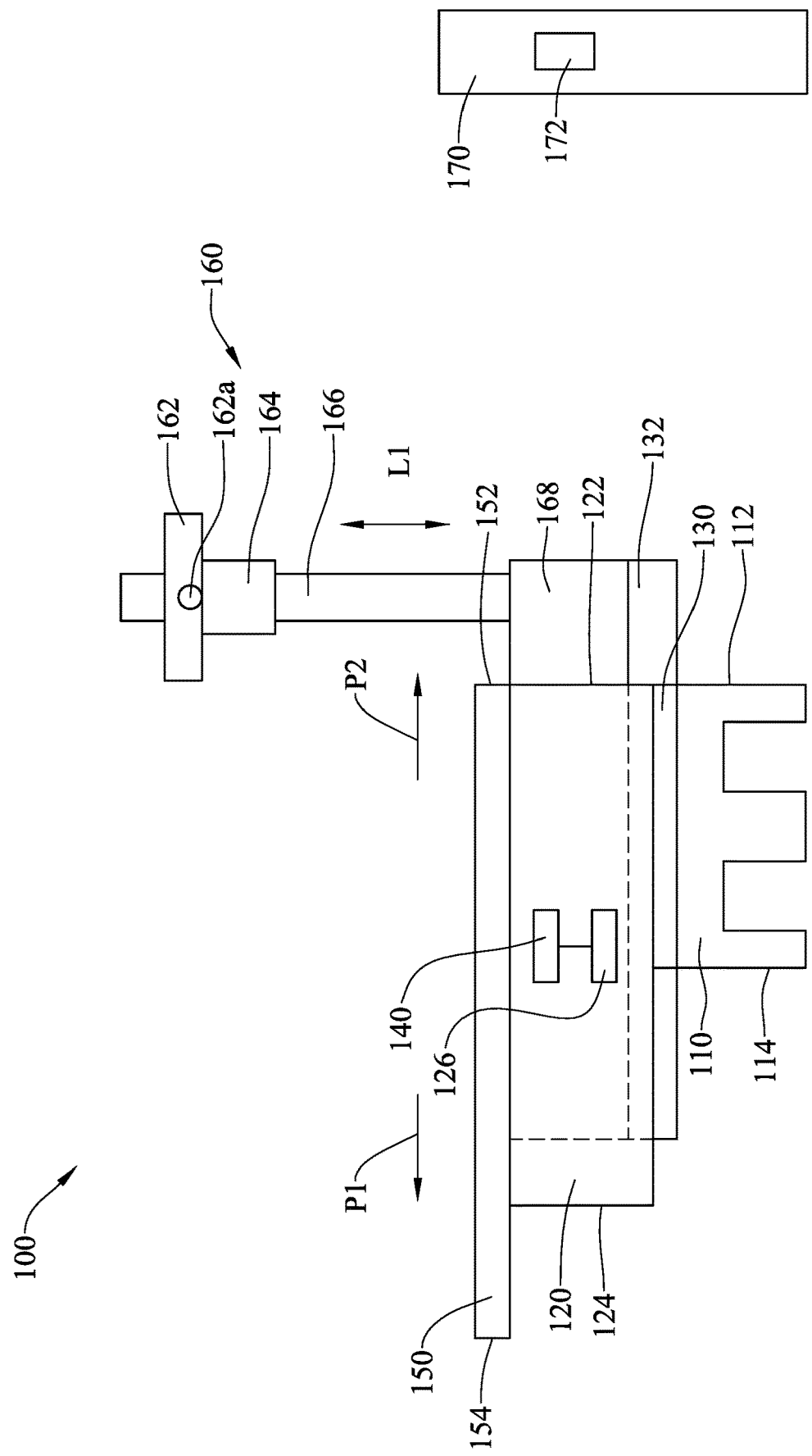
FIG. 4 shows a fourth operation state of FIG. 1.

Then, the X-ray mechanism 160 is moved toward the second base 170 in a P2 direction. Referring to FIG. 4, at this stage, the pillar 166, the collimator 164 and the X-ray tube 162a are moved synchronously toward the second base 170 in the P2 direction so as to locate the X-ray tube 162, the collimator 164 and the pillar 166 out of the lateral side 152 of the bed board 150, such that the X-ray tube 162 can perform a vertical movement L1 (as shown in FIG. 4).

Figure 5:
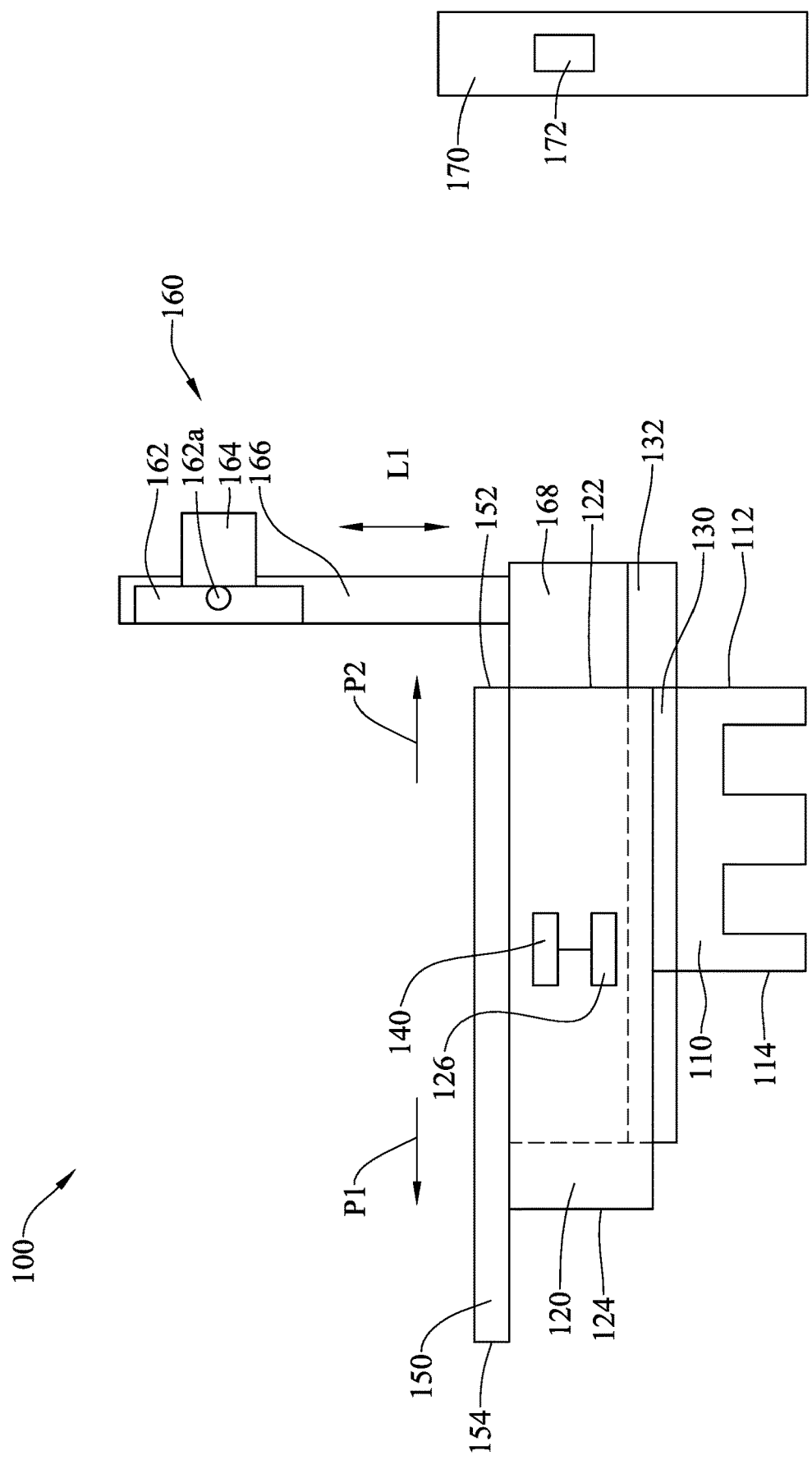
FIG. 5 shows a fifth operation state of FIG. 1.

In addition, the X-ray tube 162 and the collimator 164 are rotated to have the X-ray tube 162 and the collimator 164 to face the second base 170 (as shown in FIG. 5).

Figure 6:
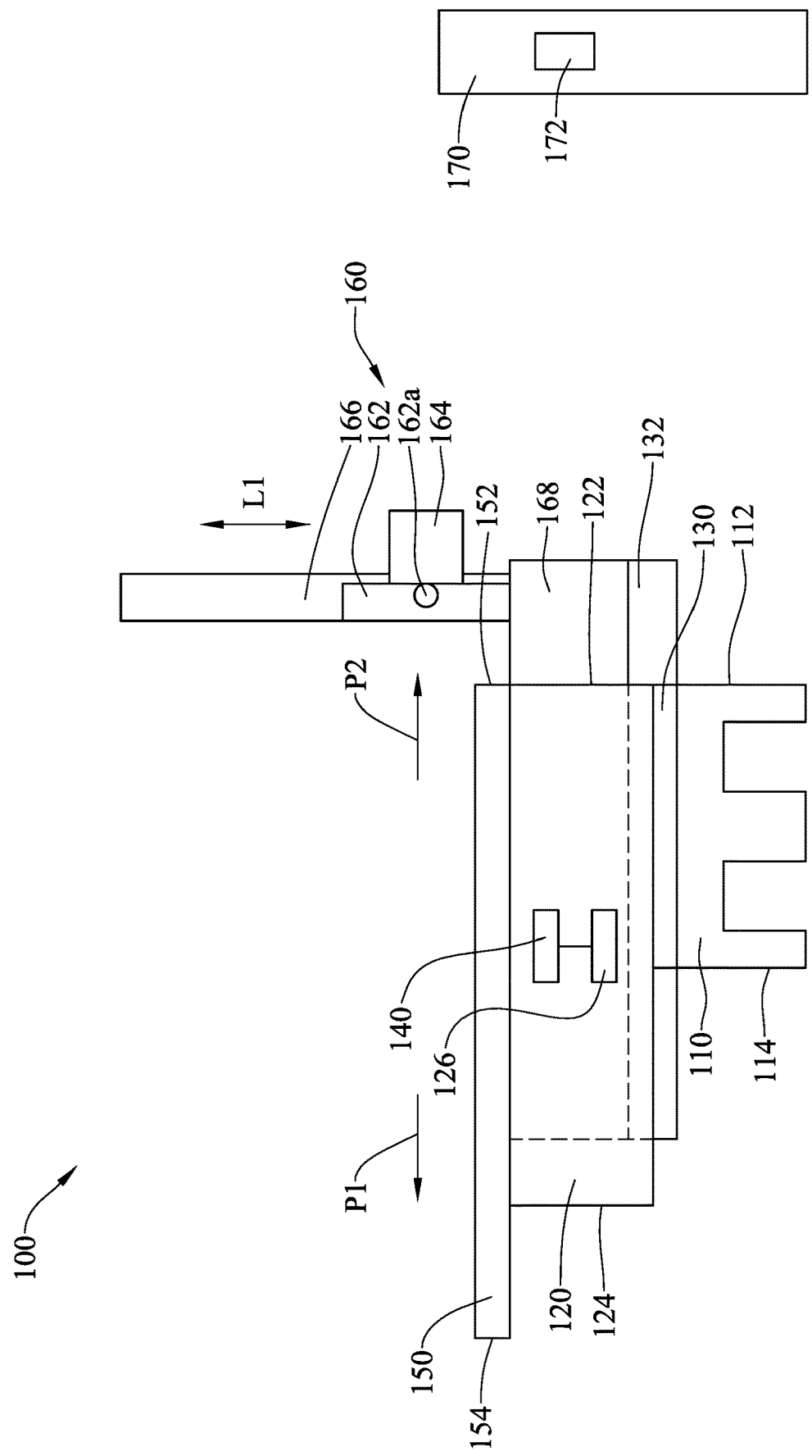
FIG. 6 shows a sixth operation state of FIG. 1.

Further, the X-ray tube 162 and the collimator 164 are lowered along the pillar 166 to be aside to the lateral side 112 of the first base 110 (as shown in FIG. 6). Namely, the X-ray tube 162 moves downward in the vertical movement L1 to a position aside to the lateral side 112 of the first base 112 by facing the second base 170.

Upon such an arrangement, a patient to be imaged at a standing position can thus be located between the X-ray mechanism 160 and the second image-receiving module 172. By moving the X-ray tube 162 to an imaging position and the second image-receiving module 172 to a corresponding image-forming position with respect to the X-ray tube 162, then, after appropriately adjusting the body position of the patient, a lateral static scan of the routine radiography upon the patient can be performed. On the other hand, in another example, the patient can be also set for a continuous X-ray motion scan. After the motion scan, a 3D image can be formed by reconstructing data collected from the motion scan (i.e. the 3D digital tomosynthesis).

In addition, if the lateral imaging mode of the scanning system 100 as shown in FIG. 6 is to be switched back to the bed-panel imaging mode, then the adjusting steps of the scanning system 100 can follow the operation states orderly from FIG. 6 to FIG. 1, such that the bed-panel imaging mode of the scanning system 100 as shown in FIG. 1 can be achieved.

In summary, the scanning system of the present invention provided above is a grounded X-ray imaging apparatus that can be easily switched to work in either the bed-panel imaging mode or the lateral imaging mode. Thereupon, clinical lying/standing scan upon the head, the neck, the body and the limbs, can be performed at the same system, either for the routine radiography or for the 3D digital tomosynthesis.

Furthermore, in the present invention, the lateral imaging mode can be achieved by moving the bed panel and the bed board to provide space for lowering the X-ray tube, and thus the aforesaid conventional shortcoming in providing the lateral imaging can be effectively resolved.

While the present invention has been particularly shown and described with reference to a preferred embodiment, it will be understood by those skilled in the art that various changes in form and detail may be without departing from the spirit and scope of the present invention.

What is claimed is:

1. A scanning system, comprising:
   a first base;
   a bed panel, including a first image-receiving module, movably located on the first base;
   a bed board, movably located on the bed panel;
   a second base, located aside to the first base, including a second image-receiving module; and
   an X-ray mechanism, movably connected with the first base, including an X-ray tube;
   wherein, by having the bed panel and the X-ray mechanism moved in opposite directions, the X-ray tube can then perform a vertical downward movement to a position below the bed board and aside to a lateral side of the first base by facing the second base.

2. The scanning system of claim 1, wherein the first base further includes a first displacement mechanism and a second displacement mechanism, the first displacement mechanism being to displace the bed panel, the second displacement mechanism being to displace the X-ray mechanism.

3. The scanning system of claim 2, wherein the first displacement mechanism and the second displacement mechanism are a pair of a sliding rail and a sliding slot.

4. The scanning system of claim 2, wherein the first displacement mechanism and the second displacement mechanism move the bed panel individually in an electrical or human-powered manner.

5. The scanning system of claim 1, wherein the X-ray mechanism further includes a bottom frame and a pillar, the pillar being connected with the bottom frame, the X-ray tube being movably located at the pillar; wherein, as the X-ray tube performs the vertical movement, the X-ray tube is lowered, along the pillar, to a position aside to the lateral side of the first base.

6. The scanning system of claim 5, wherein the X-ray mechanism further includes a collimator connected with the X-ray tube.

7. The scanning system of claim 6, wherein, as the X-ray tube performs the vertical movement, the X-ray tube and the collimator are rotated to face the second base.

8. The scanning system of claim 1, wherein the second image-receiving module is one of an upright digital flat-panel detector, an X-ray film cartridge, a digital photostimulable phosphor plate and a handheld digital flat-panel detector.

9. The scanning system of claim 1, wherein the bed panel includes a position-adjusting mechanism, the first image-receiving module being connected with the position-adjusting mechanism, the position-adjusting mechanism being connected with the bed panel, the position-adjusting mechanism being located inside the bed panel, the position-adjusting mechanism being to move the first image-receiving module, the first image-receiving module being a digital flat-panel detector.

10. The scanning system of claim 1, wherein the X-ray tube is used to perform one of a routine radiography and a 3D digital tomosynthesis.

11. The scanning system of claim 1, wherein the bed panel and the bed board are moved in a same direction.

12. The scanning system of claim 1, wherein the bed panel and the bed board are synchronously moved.

* * * * *